(12) United States Patent
Homer

(10) Patent No.: US 6,306,127 B2
(45) Date of Patent: Oct. 23, 2001

(54) METHOD FOR ALTERATION OF IRIS PIGMENTATION

(76) Inventor: Gregg S. Homer, 3329 Coy Dr., Sherman Oaks, CA (US) 91423

( * ) Notice: Subject to any disclaimer, the term of this patent is extended or adjusted under 35 U.S.C. 154(b) by 0 days.

(21) Appl. No.: 09/776,345

(22) Filed: Feb. 2, 2001

Related U.S. Application Data

(60) Provisional application No. 60/180,469, filed on Feb. 3, 2000.

(51) Int. Cl.⁷ .................................................. A61B 18/18
(52) U.S. Cl. ..................... 606/4; 606/3; 606/5; 128/898; 623/4.1; 351/159
(58) Field of Search ..................... 606/4–6; 351/160 H, 351/159, 163; 607/89; 128/898; 623/4.1

(56) References Cited

U.S. PATENT DOCUMENTS

| | | | |
|---|---|---|---|
| 5,549,596 | 8/1996 | Latina | ....................................... 606/4 |
| 6,217,171 | * 4/2001 | Auten et al. | ..................... 351/160 H |

FOREIGN PATENT DOCUMENTS

| | | | | |
|---|---|---|---|---|
| 1078604 A2 | * | 2/2001 | (EP) | .............................. A61B/18/20 |

* cited by examiner

*Primary Examiner*—Linda C. M. Dvorak
*Assistant Examiner*—A. Farah
(74) *Attorney, Agent, or Firm*—David A. Farah; Sheldon & Mak

(57) ABSTRACT

A method for altering iris pigmentation in a human, thereby altering perceived iris color of a first iris from a first iris color to a second iris color. The method comprises preselecting one or more than one laser capable of generating one or more than one laser beam which will selectively remove iris pigment of a first preselected pigment color from the first iris, and applying the one or more than one laser beam to the first iris of a first iris color to remove iris pigment of the first preselected pigment color.

12 Claims, No Drawings

METHOD FOR ALTERATION OF IRIS PIGMENTATION

CROSS-REFERENCE TO RELATED APPLICATION

The present Application claims the benefit of U.S. provisional patent application No. 60/180,469, filed Feb. 3, 2000, entitled "Method for Alteration of Iris Pigmentation," the contents of which is incorporated herein by reference in their entirety.

BACKGROUND

Eye color in humans varies widely between ethnic groups and between individuals. Perceived eye color of a normal human is dependent on the presence of several colored pigments in the iris which are coded for by different genes.

Iris color plays and has played a significant social function as an attribute of beauty. In recent years, alteration of some types of iris color has become possible through the use of colored contact lenses. Such colored contact lenses can have a prescriptive optical power, or can be optically neutral such that the lenses serves a cosmetic function only.

There are several disadvantages associated with the use of colored contact lenses for cosmetic purposes. First, the lenses have the same potential complications of use as contact lenses with prescriptive optical powers, including allergic reactions to the lens material and infections from improper handling. Further, contact lenses cannot be tolerated by some potential users due to the discomfort. Additionally, colored contact lenses require a degree of dexterity to insert and remove that is not possessed by all potential users. Further, permanent changes in iris color cannot be achieved through the use of colored contact lenses.

Another method for altering iris color involves the use of colored lens implanted anterior to the iris. Such implants require an invasive procedure to place the lens in position. Because of the potential complication of an invasive procedure and of leaving a foreign body within the eye, the implantation of color lenses has not become a widely adopted procedure.

Therefore, there remains a need for a method to alter iris pigmentation in a human which does not require colored contact lenses or implanted lenses. Additionally, there remains a need for a method to alter iris pigmentation in a human which can permanently alter iris color.

SUMMARY

According to one embodiment of the present invention, there is provided a method for altering iris pigmentation in a human, thereby altering perceived iris color of a first iris from a first iris color to a second iris color. The method comprises preselecting one or more than one laser capable of generating one or more than one laser beam which will selectively remove iris pigment of a first preselected pigment color from the first iris, and then applying the one or more than one laser beam to the first iris of a first iris color to remove iris pigment of the first preselected pigment color. The removal of the iris pigment of the first preselected color causes an alteration in the color of the first iris from the first iris color to the second iris color.

In a preferred embodiment, the second iris color is a different hue than the first iris color. In another preferred embodiment, the second iris color is substantially the same hue as the first iris color but less saturated than the first iris color. In another preferred embodiment, the second iris color is substantially a different hue than the first iris color and less saturated than the first iris color. In yet another preferred embodiment, the hue of the second iris color is a hue that does not naturally occur in a human iris.

In a preferred embodiment, the method further comprises creating an opening in the cornea of the human before applying the one or more than one laser beam, and then applying the one or more than one laser beam through the opening. In another preferred embodiment, the one or more than one laser preselected is a pulse dye laser. In a particularly preferred embodiment, the one or more than one laser beam generated has a wavelength of between about 300 nm and about 900 nm.

In another preferred embodiment, the method further comprises altering iris pigmentation in the human, thereby altering perceived iris color of a second iris from a third iris color to a fourth iris color. The method comprises preselecting one or more than one laser capable of generating one or more than one laser beam which will selectively remove iris pigment of a second preselected pigment color from the second iris and applying the one or more than one laser beam to the second iris of the third iris color to remove iris pigment of the second preselected pigment color. The removal of the iris pigment of the second preselected color causes an alteration in the color of the second iris from the third iris color to the fourth iris color. The second iris color can be substantially same as the fourth iris color or can be substantially different than the fourth iris color.

The method of the present invention can be repeated to alter iris pigmentation further as desired.

DESCRIPTION

According to one embodiment of the present invention, there is provided a method for altering iris pigmentation in a human, and thereby altering perceived iris color from a first iris color to a second iris color. In one embodiment, the method comprises preselecting one or more than one laser capable of generating one or more than one laser beam which will selectively remove iris pigment of a first preselected pigment color. Next, the one or more than one laser beam is applied to an iris of a first iris color to remove iris pigment of the first preselected pigment color. The removal of the iris pigment of the first preselected pigment color causes an alteration in the color of the iris from the first iris color to the second iris color, where the second iris color is a different hue than the first iris color.

According to another embodiment of the present invention, there is provided a method for altering the iris pigmentation in the iris of a human to change the color of the iris from a first iris color to a second iris color, where the second iris color is perceived as substantially the same hue as the first iris color but less saturated than the first iris color. The method comprises preselecting one or more than one laser capable of generating one or more than one laser beam, where the one or more than one laser beam will selectively remove iris pigment. The one or more than one laser beam is applied to an iris of the first iris color to remove iris pigment, where the removal of the iris pigment causes an alteration in the color of the iris from the first iris color to the second iris color. The second iris color is perceived as substantially the same hue as the first iris color but less saturated than the first iris color.

According to another embodiment of the present invention, there is provided a method for altering iris pigmentation in a human, and thereby altering perceived iris color from a first iris color to a second iris color, where the second iris color is both a different hue and less saturated than the first iris color. In one embodiment, the method comprises preselecting one or more than one laser capable of generating one or more than one laser beam which will selectively remove iris pigment of a first preselected pigment color. Next, the one or more than one laser beam is applied to an iris of a first iris color to remove iris pigment of the first preselected pigment color. The removal of the iris pigment of the first preselected pigment color causes an alteration in the color of the iris from the first iris color to the second iris color.

The method of the present invention can further include creating an opening in the cornea of the human before applying the one or more than one laser beam, and then applying the one or more than one laser beam through the opening.

The use of lasers to remove iris pigmentation is advantageous because specific lasers can be selected which create laser beams which are selectively absorbed by iris pigment of specific colors. This property allows the selection of lasers to selectively destroy iris pigment of specific colors while not destroying iris pigment of other colors. For example, the laser beam generated could be selected to remove yellow or red pigment from the iris only.

In a preferred embodiment, the one or more than one laser selected is a pulse dye lasers because the wavelength of the laser beam is determined by the color of the material through which the laser beams pass. This advantageously increases the specificity of iris pigment destruction by the laser beams by selecting appropriate dyes. Moreover, the intensity of the laser beams can be adjusted to minimize damage to ocular tissue and iris pigments that are not specifically targeted. In another preferred embodiment, the one or more than one laser is a pulse dye laser and the wavelength generated by the one or more than one laser is between about 300 nm and about 900 nm. For example, suitable lasers includes the Due-220, DUO-221, and the DUO-210 models, as well as the DYE 120, the DYE 121, and the DYE 110 models ( Laser Science, Inc., Franklin, Mass. US).

In another preferred embodiment, the one or more than one laser selected is a modified excimer laser which permits the operator to alter the nature and quantity of the material through which the laser beam passes. Preferably, the one or more than one excimer laser will generate a wavelength of between about 100 nm and 250 nm. For example, the ArF excimer laser used in ophthalmic photoablation produces a beam of ultraviolet light with a wavelength of 193 nm. The ArF excimer laser beam passes though a specified quantity of argon fluoride, and both the material and its quantity can be modified to achieve the desired wavelength. Additionally, LaserSight Technologies, Inc. (Winter Park, Fla. US) has devised two solid state lasers: the LaserHarmonic-1 and LaserHarmonic-2. The LaserHarmonic-1 is flash lamp pumped and employs the fifth harmonic of a Nd:Yag at 213 nm. The LaserHarmonic-2 is a diode pumped fifth harmonic Nd:YLF laser at 209 nm. While a pulse dye laser or an excimer laser are preferred, other lasers can be used in the present method.

The methods of the present invention are performed as follows. First, the patient is examined and a determination is made in consultation with the patient as to the eye color the patient prefers to have. Next, it is determined whether the eye color the patient prefers to have is obtainable using the methods of the present invention by virtue of laser alteration of the patient's existing iris pigmentation. For example, if the patient has brown irises and prefers to have green irises, then laser alteration of the patient's iris pigment to result in green irises is possible. If the patient prefers to have his present brown irises altered to a lighter shade of brown, then laser alteration of the patient's iris pigment to result in lighter brown irises is possible. Further, if the patient prefers to have his present brown irises altered to a lighter shade of green, then laser alteration of the patient's iris pigment to result in lighter green irises is possible. If, however, the patient has blue irises and prefers to have brown irises, then laser alteration of the patient's iris pigment to result in brown irises is not possible.

Further, it is possible using methods according to the present invention to alter iris pigmentation of a patient to result in an iris color which is not naturally occurring, such as violet, or to alter iris pigment differently between two eyes of a patient to result in the patient having irises of different colors by differentially treating each iris of a patient according to one method of the present invention or by treating only one iris of the patient according to the present invention.

Next, one or more than one laser is selected which will alter the iris pigment of the patient in an appropriate manner to achieve the desired iris color change. If a pulse dye laser is used, a dye filter is selected which will selectively destroy iris pigment of specific colors. Then, the intensity of the laser beam is set to a level that minimizes the damage to any ocular tissue while still allowing removal of the required iris pigmentation. Optionally, an incision is made into the cornea prior to application of the laser.

The one or more than one laser beam is then applied to the iris pigment for a sufficient time to effect removal of the unwanted iris pigment. The remaining pigment then leaves the iris with the desired color. If more than one laser beams are used, the laser beams can be applied sequentially or simultaneously. If necessary, a temporary contact lens can be applied to reduce post-procedure discomfort.

Additionally, the method of the present invention can be repeated at a time spaced away from the original application of the one or more than one laser, in order to further alter the iris pigmentation, after allowing the iris and associated tissue to heal from the original application.

EXAMPLE I

One method of the present invention is performed as follows. An adult male patient is selected who desires to change his brown eye color to green. He is found in satisfactory general and ocular health. After being counseled regarding the procedure and being prepared, a suitable laser is applied to each iris through the patient's intact corneas to remove red pigment present in his irises until the remaining iris pigment is perceived to render his irises green.

Although the present invention has been discussed in considerable detail with reference to certain preferred embodiments, other embodiments are possible. Therefore, the scope of the appended claims should not be limited to the description of preferred embodiments contained in this disclosure.

I claim:

1. A method for altering iris pigmentation in a human, thereby altering perceived iris color of a first iris from a first iris color to a second iris color, the method comprising:

a) preselecting one or more than one laser capable of generating one or more than one laser beam which will selectively remove iris pigment of a first preselected pigment color from the first iris; and b) applying the one or more than one laser beam to the first iris of a first iris color to remove iris pigment of the first preselected pigment color;

where the removal of the iris pigment of the first preselected color causes an alteration in the color of the first iris from the first iris color to the second iris color.

2. The method of claim 1, where the second iris color is a different hue than the first iris color.

3. The method of claim 1, where the second iris color is substantially the same hue as the first iris color but less saturated than the first iris color.

4. The method of claim 1, where the second iris color is substantially a different hue than the first iris color and less saturated than the first iris color.

5. The method of claim 1, where the hue of the second iris color is a hue that does not naturally occur in a human iris.

6. The method of claim 1, where the one or more than one laser preselected is a pulse dye laser.

7. The method of claim 1, where the one or more than one laser beam generated has a wavelength of between about 300 nm and about 900 nm.

8. The method of claim 1, further comprising altering iris pigmentation in the human, thereby altering perceived iris color of a second iris from a third iris color to a fourth iris color, the method comprising:

a) preselecting one or more than one laser capable of generating one or more than one laser beam which will selectively remove iris pigment of a second preselected pigment color from the second iris;

b) applying the one or more than one laser beam to the second iris of the third iris color to remove iris pigment of the second preselected pigment color;

where the removal of the iris pigment of the second preselected color causes an alteration in the color of the second iris from the third iris color to the fourth iris color.

9. The method of claim 1, further comprising repeating steps a) and b).

10. The method of claim 1, further comprising creating an opening in the cornea of the human before applying the one or more than one laser beam, and then applying the one or more than one laser beam through the opening.

11. The method of claim 10, where the second iris color is substantially same as the fourth iris color.

12. The method of claim 10, where the second iris color is substantially different than the fourth iris color.

* * * * *